United States Patent [19]

Brunke et al.

[11] Patent Number: 5,492,887

[45] Date of Patent: Feb. 20, 1996

[54] 8-EXO-FORMYL-2,6-EXO-TRICYCLO(5.2.1.0²,⁶)DECANE, METHOD OF PREPARING IT AND USE OF THE SAME

[75] Inventors: Ernst-Joachim Brunke; Claus-Hermann Kappey, both of Holzminden; Bernd Hölscher, Halle; Hartmut Struwe, Höxter/Stahle, all of Germany

[73] Assignee: Dragoco Gerberding & Co. GmbH, Holzminden, Germany

[21] Appl. No.: 960,431

[22] PCT Filed: Apr. 10, 1992

[86] PCT No.: PCT/DE92/00307

§ 371 Date: Dec. 11, 1992

§ 102(e) Date: Dec. 11, 1992

[87] PCT Pub. No.: WO92/18451

PCT Pub. Date: Oct. 26, 1992

[30] Foreign Application Priority Data

Apr. 12, 1991 [DE] Germany ............ 41 12 093.0

[51] Int. Cl.⁶ .................................................. A61K 7/46
[52] U.S. Cl. ............... 512/16; 568/445; 568/443; 568/444
[58] Field of Search .................. 508/445, 443, 508/444; 512/16

[56] References Cited

U.S. PATENT DOCUMENTS

| | | | |
|---|---|---|---|
| 3,270,061 | 8/1966 | Chodroff et al. | 568/445 |
| 4,225,515 | 9/1980 | Weber et al. | 568/445 |
| 4,229,324 | 10/1980 | Takaishi et al. | 568/445 |
| 4,319,049 | 3/1982 | Rogier | 568/445 |
| 4,541,949 | 9/1985 | Sprecker et al. | 568/445 |
| 4,762,819 | 8/1988 | Brunke | 568/445 |

OTHER PUBLICATIONS

European Patent Office Search Report, dated Jun. 20, 1992, by Examiner J. C. Henry.

*Primary Examiner*—James H. Reamer
*Attorney, Agent, or Firm*—Dominik & Stein

[57] ABSTRACT

It was found that 8-exo-formyl-2,6-exo-tricyclo[5.2.1.0²,⁶] decane having the constitution and stereochemistry of formula (I) possesses particularly useful olfactory properties which are clearly superior to those of the 8-endo-epimer and which already have an effect if compound (I) is enriched with mixtures of 8-exo- and 8-endo-epimers. Compound (I) can therefore be advantageously used, in pure or enriched form, as a scent or as a component of perfume compositions. To prepare an enriched epimer mixture, a mixture obtained in a known manner (U.S. Pat. No. 3,270,061) and having an exo/endo ratio of 1.45:1 is brought into equilibrium by base catalysis, preferably by the action of alkali hydroxides in alcoholic solution, to give an exo/endo ratio of 5.25:1. Alternatively, the enriched epimer mixture can be prepared starting from 8-formyl-2,6-exo-tricyclo[ 5.2.1.0²,⁶]decene-3(4), catalytically hydrogenated for example with palladium coal and then optionally brought into equilibrium. Or 2,6-exo-tricyclo[5.2.1.0²,⁶]decene-8 can be hydroformylated and also optionally brought into equilibrium. The pure compound (I) is prepared by reducing preferably a mixture of 8-exo- and 8-endo-epimers obtained in the manner known per se to a mixture of the corresponding alcohols, from which the 8-exo-configured methylol is isolated by chromatography or distillation and oxidized to obtain the aldehyde (compound I) again.

13 Claims, No Drawings

8-EXO-FORMYL-2,6-EXO-TRICYCLO(5.2.1.0²,⁶) DECANE, METHOD OF PREPARING IT AND USE OF THE SAME

This appln. is a PCT of 371 of DE92/00,307 filed Apr. 10, 1992, pending.

In modern industrial perfumery there ms a permanent demand for new scent products having, in addition to high stability and hence varied technical possible applications, scent notes that are as original and aesthetic as possible. An additional factor in the industrial production of scents is the provision of such new scents which, starting from synthetic raw materials, are available in large quantities and cheaply.

The present invention relates to 8-exo-formyl-2,6-exo-tricyclo[ 5.2.1.0²,⁶]decane (1) which is a valuable new scent either in its pure form or in an enriched form together with its 8-endo-isomer 2.

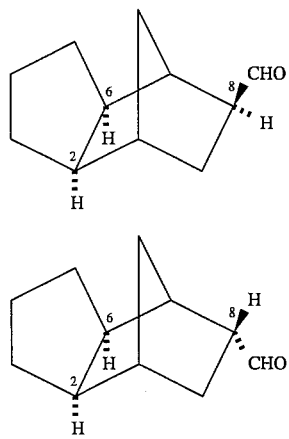

It is novel that the aldehyde 1 having the constitution and stereochemistry shown not only results in particularly positive scent characteristics but also that it is of particular industrial value owing to its behavior in perfume-technical applications. The compound 1 having the constitution shown and the analogous configuration has not yet been described.

C-8-substituted tricyclo[5.2.1.0²,⁶]decane-derivatives without a statement relating to the stereochemistry at position C-8 are described in U.S. Pat. No. 3,270,061 (Aug. 30, 1966). Among those is also the 8-formyl compound D which, however, is not mentioned in the claims of the above mentioned patent.

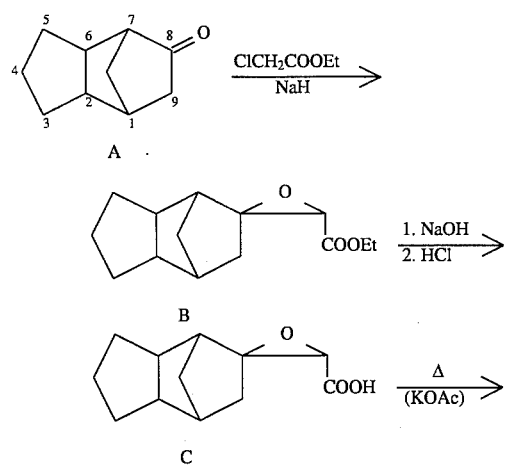

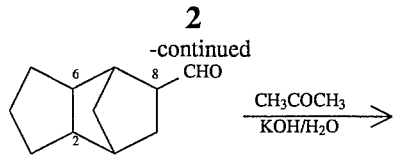

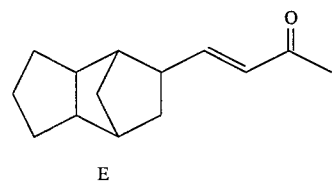

In this description, the stereochemistry of the ring system is described as 2,6-exo. However, this is not considered as being relevant for the scent characteristics of the mentioned or claimed compounds. In the above mentioned patent in column 1, lines 69 to 72 there is a statement that the compounds described usually and preferably consist of the 2,6-exo-isomers and that the corresponding endo-isomers could, however, be used in the same way in accordance with the invention therein. There is also no statement about the possible importance of the C-8 stereochemistry. It is therefore novel and surprising that the aldehyde 1, meaning exclusively the 2,6 exo-configuration, with the exo-configuration of the formyl group at the C-8, provides a scent which is characterised by a particularly natural and aesthetically valuable green note.

For the aldehyde D of the same constitution which has been obtained in accordance with the U.S. Pat. No. 3,270,061 an intensive green note having earthy top-notes is mentioned (column 5, lines 69 to 71). In this patent specification, it is also stated that the aldehyde D is of value for the formulation of heavy flowery notes, such as violet notes. However, in the U.S. patent, aldehyde D has not been claimed as a scent. In contrast, only ketones E which are produced by consecutive reactions have been claimed and their scent characteristics have been extensively described. One can presume that owing to its earthy bynote aldehyde D was only of a limited value and hence has not found entry into the international perfumery.

The aldehyde D can be produced by analogy to U.S. Pat. No. 3,270,061 from the tricyclic ketone A (TCD-ketone A, commercial product of the firm Hoechst, Germany): by conversion with ethyl chloro-acetate in the presence of sodium hydride the glycidic ester B is obtained; the saponification of B results in the glycidic acid C which also could be converted into the aldehyde D by heating with potassium acetate. By reproducing the prescription given in U.S. Pat. No. 3,270,061 we obtained the aldehyde D at a purity of about 99% (Example 1). The known scent characteristics could be confirmed by us. Surprisingly, we have now found that under the effect of acids or bases, preferably of alkaline hydroxides or alkaline carbonates in an alcoholic solution, a clear improvement of the scent of aldehyde D can be noticed. The scent of the treated material is not only clearly stronger, but also more naturally green.

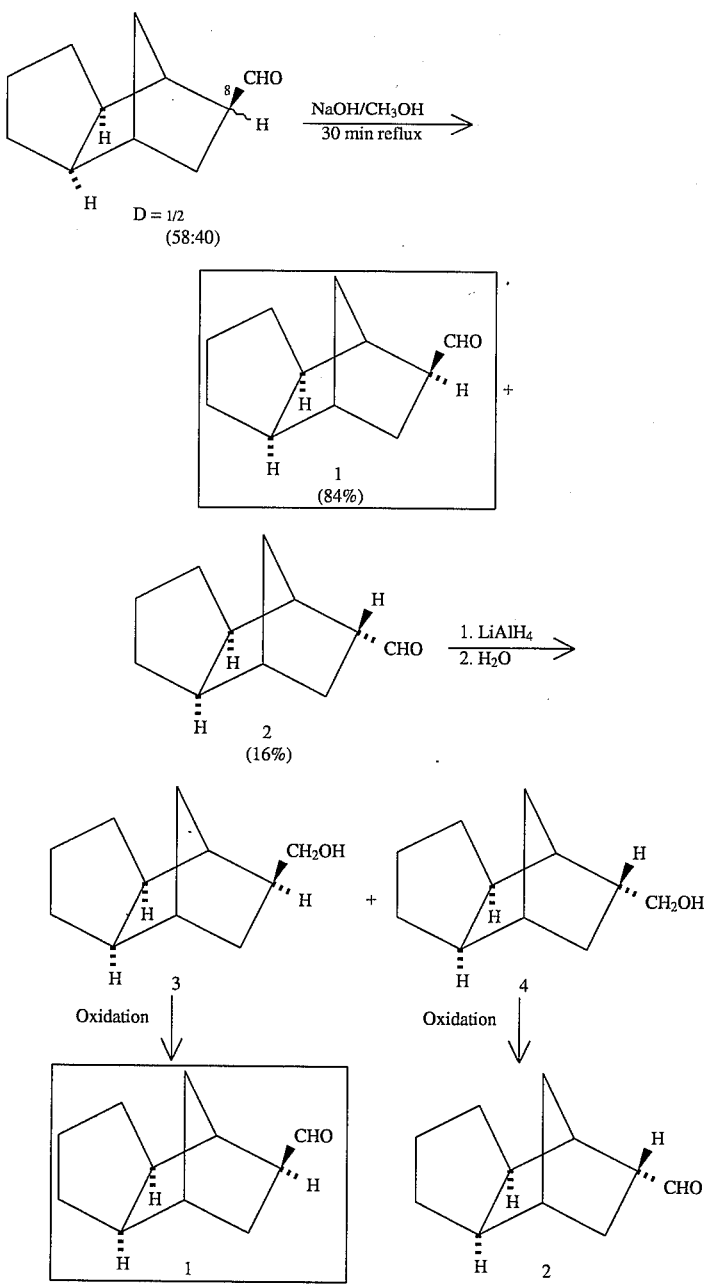

The analysis of the aldehyde D produced analogously to U.S. Pat. No. 3,270,061 for the presence of other compounds after the treatment with acids or bases is difficult even using modern analytical methods. The material produced in accordance with U.S. Pat. No. 3,270,061 (Example 1) was in our hands uniform when analysed by gas chromatography. After base treatment (Example 3a), no peak separation can be observed even using highly effective quartz capillary columns; accordingly, the material must be unchanged. In order to clarify the olfactory differences observed for the aldehyde, which presumably was present as a mixture, we produced the corresponding alcohol mixture in a known way by reduction with lithium aluminum hydride. In this process other reducing agents such as sodium borohydride or even catalytic methods can be used. Surprisingly it has been found that by the reduction, an alcohol mixture had been formed which could be separated by chromatography. This was visible, amongst other means, by clearly differing gas chromatographic retention times and significantly differing mass spectra. By separation using distillation or chromatography, alcohols 3 and 4 have been isolated and characterised spectroscopically.

By reduction of the stereo-isomeric aldehyde mixture to the alcohol mixture, its separation by physical methods followed by an oxidation, 8-exo-formyl-2,6-exo-tricyclo[5.2.1.0$^{2,6}$]decane (1) and its 8-endo-formyl-isomers are obtainable in pure form. It was not possible to directly separate the stereo-isomeric aldehyde ½ by chromatography or by distillation. The stereo-isomerically pure aldehyde ½ can be equilibrated by the action of acids or bases, preferably by methanolic caustic soda. The exo/endo-isomer ratio at the C-8 is 84:16 in an equilibrated mixture. The aldehyde mixture according to the U.S. Pat. No. 3,270,061 had a 58:40 ratio of the exo/endo isomer at the C-8, as determined by us by reduction of the alcohol mixture followed by the determination of the isomers using gas chromatography. Under equilibrium conditions we could also obtain from this isomeric mixture a product having an 8-exo/endo-ratio of 84:16. The effect of strong bases, in particular of alkaline hydroxides in alcohol solutions, increases the C-8-exo/endo-ratio from 1.45:1 to 5.25:1. Therefore, this can be used to enrich the stereoisomer that is olfactorily preferred.

The glycidic ester synthesis with TCD-ketone A (A) can be in the presence of antioxidants such as phenothiazine in pyridine with concomitant use of sodium methylate (Example 3b). In a one-pot reaction the saponification to the glycidic acid can be performed using methanolic caustic soda and the carboxylation resulting in the conversion of the aldehyde can be performed using acetic acid (that is in the presence of sodium acetate).

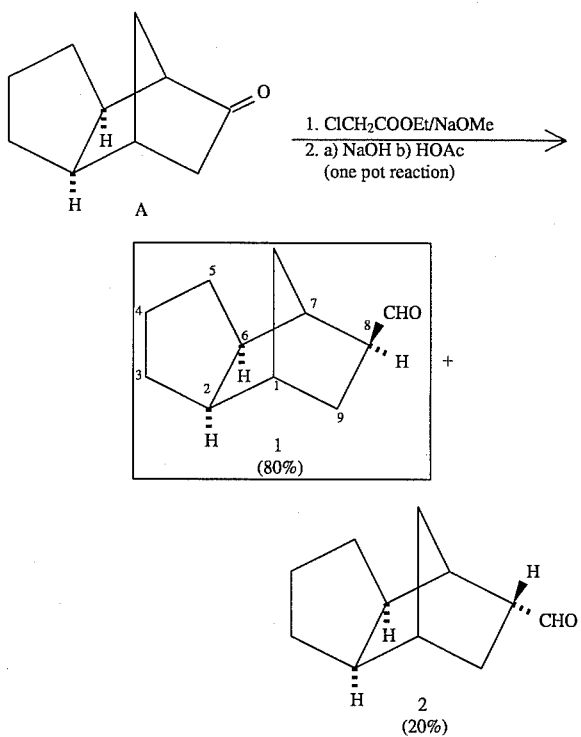

The performance of the reaction sequence as a one-pot reaction results in relatively low production costs. The pH-calibration during the decarboxylation and the processing determines the ratio of isomers of the C-8-formyl-group (C-8-exo/endo= 80:20). The raw-aldehyde mixture produced according to this process still contains a small residual amount of the starting material TCD-ketone A. The C-8-exo-enriched aldehyde mixture ½ (80:20) can be isolated in a highly pure form via its bisulphite adduct.

An alternative synthesis sequence starts with the 2,6-exo-dicyclo-pentadiene (5) which can be converted into the unsaturated aldehyde mixture 6 by selective hydroformylation at the more reactive double bond at the norbornene part of the 2,6-exo-dicyclo-pentadiene. The catalytic hydrogenation of 6 results in the aldehyde mixture ½ of an C-8-exo/endo ratio of 4.3:1. Such region-selective hydroformylations are, for example, described in DE-A 3447030. The catalytic hydrogenation of the unsaturated aldehyde mixture 6 is preferably performed using palladium carbon under controlled reaction conditions.

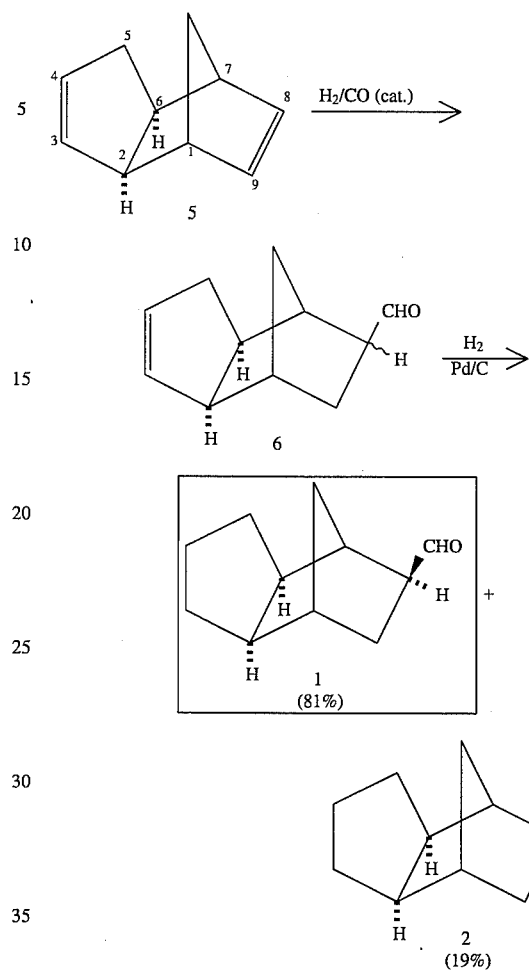

A further alternative reaction path starts from the 2,6-exo-tricyclo[ 5.2.1.0$^{2,6}$]decene-8 (7), hydroformylation of which directly results in the aldehyde mixture ½ which again can be converted into the stereo-isomer mixture ½ with a high proportion of 8-exo by equilibration.

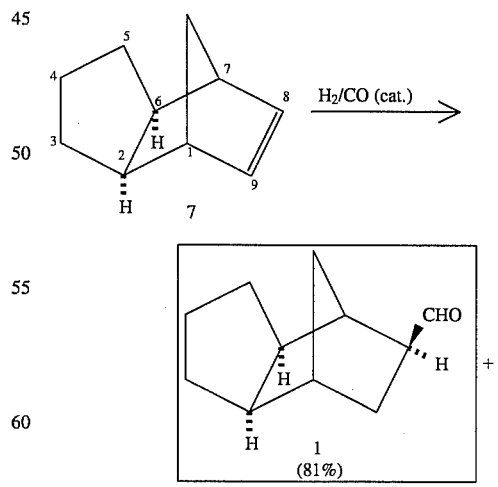

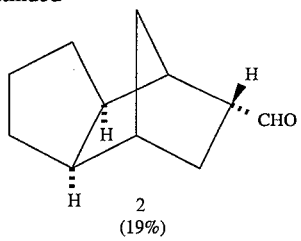

2
(19%)

The 8-exo-formyl-2,6-tricyclodecane (1) is distinguished from its C-8-epimers 2 by especially advantageous scent characteristics. The olfactory value of compound 1 also manifests itself in the mixtures of the diastereomers 1 and 2 if 1 is enriched, preferably to at least 70% compared to 30% of compound 2. The scent note of compound 1 can be described as fresh-green and that of compound 2 as earthy, musty, green. Compound 1 not only is distinguished from the stereo-isomeric compound 2 by a more advantageous note of scent, but also by a clearly larger strength of scent. In perfume compositions, the olfactory value of compound 1 in a pure or in an enriched form (½=70:30) stands out even at a relatively low dosage (see Examples 8, 9, 10). An enrichment of the 8-exo-isomer 1 by even 10% when compared to the prior art led to a clear improvement of the scent effect in the perfume arrangement according to Example 8. This clear and positive effect is reinforced by further enrichment of compound 1. The excellent stability and substantivity of compound 1 in a pure or in an enriched form and the positive scent characteristics described have the result that compound 1 in a pure or in an enriched form is a new and valuable scent.

EXAMPLE 1

Production of 8-exo/endo-formyl-2,6-exo-tricyclo[5.2.1.0$^{2,6}$]decane (D =½) according to U.S. Pat. No. 3,270,061 a) column 4, lines 26–66; b) column 5, lines 19–65)

a) Production of glycidic esters B from ketone A

To a solution of 270 g (1.8 mol) TCD-ketone-A (A) and 245.2 g (2 mol) ethyl chloro-acetate in 900 ml of absolute toluene was mixed gradually 60 g (2 mol) of 80% sodium hydride-dispersion in mineral oil over a 3 h period at 30° to 35° C. under stirring, whereby cooling with ice water was necessary owing to the exothermic reaction. After an additional hour of stirring at 30° to 35° C. the exothermic reaction ceased. Thereafter, the reaction mixture was stirred overnight without further cooling. The excess of sodium hydride was then neutralised by the careful addition of 50 ml methanol. The reaction mixture was diluted with 500 ml water and rendered slightly acidic by the addition of 15 ml of glacial acetic acid. After removal of the organic phase the aqueous phase was extracted with 150 ml toluene. The combined toluene phases were washed with a NaHCO$_3$ solution and water until they were neutral and then, the solvent was removed in a 20 mm vacuum. The remaining raw product (412.9 g) was distilled through a 20 cm Vigreux column. The yield was 302,6 g glycidic ester B in the boiling range of 139°–145° C./1.5 mm. Gas chromatogram (30 m DBWAX, 100°– 240° C., 6° C./min: t$_R$=15.3 (20.4%), 15.7 (29.5%), 16.2 (20.3%), 16.9 min. (28.0%).

b) Production of aldehyde D via glycidic acid C

A solution of 118 g (0.5 mol) glycidic ester B in 275 ml methanol was mixed under stirring over a 30 min period with a solution of 40 g NaOH (1 mol) in 350 ml H$_2$O, whereby cold water cooling was necessary owing to the slightly exothermic reaction. Thereafter, the mixture was stirred for 17 h without further cooling. Using a solution of 112 g conc. HCl in 250 ml H$_2$O the mixture was acidified to pH=3 and then extracted twice with 150 ml toluene. The toluene extract was washed with water up to pH=5.5 and then the solvent was removed in a 20 mm vacuum. 98.5 g raw glycidic acid C was obtained as a residue which was heated after addition of 3 g potassium acetate under vacuum. The product so formed is then distilled through a 20 cm Vigreux-column. 71.5 g of aldehyde D (62% of the theory [th.] relative to the TCD-ketone-A (A)) in the boiling range of 82°–87° C./1.5–2 mm were obtained as a colorless oil.

Gas chromatogram (30 m DBWAX, 100°–240° C., 6° C./min): t$_R$=13.0 min (98.6%).

Refractive index: n$_D^{20}$=1.5020 (Lit.:n$_D^{20}$=1.4999)

Density D$_4^{20}$=1.0376

EXAMPLE 2 a) Reduction of the aldehyde mixture D (½) from Example 1

A solution of 8.2 g (50 mmol) of aldehyde D from Example 1 in 20 ml abs. diethyl ether was dropped into a suspension of 570 mg (15 mmol) LiAlH$_4$ in 10 ml abs. diethyl ether at 0° C. under stirring and cooling. Thereafter, it was stirred over a period of 30 min at room temperature, and the surplus of LiAlH$_4$ was neutralised by the addition of 1 ml ethyl acetate. It was then hydrolysed with 5 ml of ice water and the resulting suspension was filtered over theorite. The filtrate was stripped of the solvent in a 20 mm vacuum. 8.2 g of the alcohol mixture ¾ was obtained as a colorless oil.

Gas chromatogram (30 In DBWAX, 100°–240° C., 6° C./min):

t$_R$=17.8 (40% endo-isomer), 18.3 min (58%, exo-isomer)

b) Separation of the alcohol mixture ¾

82 g of the alcohol mixture ¾ having the composition mentioned above and being obtained by reduction of the corresponding amount of aldehyde D from Example 1 were subjected to fractional distillation at 110°–111° C. and to a 1 m spinning band column at 3.5 mbar. 37.9 g distillate were obtained wherein the more volatile endo-isomer 4 was enriched to 80.6%. Additionally 40.8 g of distillate residue were obtained in which the exo-isomer 3 was enriched to 95.1%. By renewed distillation of the distillate or a continued distillation of the distillation residue using a 1 m spinning band column, the endo-isomer 4 and the exo-isomer 3 were obtained in a purity of 98.3% and 99.6% respectively.

exo-isomer 3

IR (film): v=3329, 2937, 1478, 1451, 1078, 1034, 994 cm$^{-1}$.

$^1$H-NMR (300 MHz, CDCl$_3$): δ=0.8–1.05 (m, 4 H), 1.09–1.32 (m, 3H), 1.51–1.67 (m, 2H), 1.72–1.90 (m, 4H), 1.94 ("s", 2H), 2.05 (br. s, 1H, OH), 3.33–3.43 ppm (m, 2H, CH$_2$OH).

$^{13}$C-NMR (125.7 MHz, CDCl$_3$): δ=27.4 (t), 29.1 (t), 32.0 (t), 32.4 (t), 33.1 (t), 40.6 (d), 42.4 (d), 44.4 (d), 47.8 (d), 48.5 (d), 66.5 ppm (t).

MS: m/z (%)=166 (0.4, M$^+$) 148 (12), 135 (100), 107 (19), 93 (16), 91 (16), 81 (13), 80 (18), 79 (37), 78 (11), 77 (14), 67 (47), 66 (10), 41 (18), 39 (14), 31 (15).

endo-isomer 4

IR (film): ν=3316, 2958, 1475, 1452, 1070, 1056, 1035, 1014, 991 cm$^{-1}$.

$^1$H-NMR (300 MHz, CDCl$_3$): δ=0.50–0.56 (m, 1H), 0.86–1.05 (m, 3H), 1.07–1.25 (m, 1H), 1.40–1.46 (m, 1H), 1.58–1.74 (m, 3H), 1.77–1.94 (m, 3H), 1.96–2.11 (m, 3H), 2.22 (br. s, 1H, OH), 3.48–3.60 (m, 2H, CH$_2$OH).

$^{13}$C-NMR (125.7 MHz, CDCl$_3$): δ=27.1 (t), 32.2 (t), 32.7 (t), 32.8 (t), 33.7 (t), 40.2 (d), 41.1 (d), 41.9 (d), 42.1 (d) 48.4 (d), 64.2 ppm (t).

MS: m/z (%)=166 (0.8, M$^+$), 148 (25), 135 (85), 133 (31), 120 (45), 119 (92), 107 (47), 106 (34), 105 (25), 95 (35), 94 (31), 93 (34), 91 (48), 81 (34), 80 (52), 79 (100), 78 (20), 77 (30), 67 (72), 66 (23), 41 (28), 39 (22), 31 (21).

EXAMPLE 3

Production of 8-exo/endo-formyl-2,6-exo-tricyclo[5.2.1.0$^{2,6}$]decane (½) having an increased content of 8-exo-isomer 1 (starting from the TCD-ketone A)

Equilibration of the 8-exo/endo-aldehyde mixture D (½) from Example 1

5 g of the aldehyde D from Example 1 (exo/endo=58:40) was dissolved in a mixture of 1 g 50% caustic soda and 25 g of methanol and was heated for a period of 30 min under reflux. After cooling the mixture was acidified with 1 g glacial acetic acid and the methanol was removed by distillation in a pre-vacuum. The residue was mixed with 25 g H$_2$O and extracted with diethyl ether. The ether-containing extract was neutralised by washing with a saturated NaHCO$_3$ solution and a 5% NaCl-solution, dried over Na$_2$SO$_4$, and the solvent was removed in a 20 mm vacuum. After bulb tube distillation of the residue (4.95 g) under a 2 mm vacuum, 4.85 g of the product were obtained as a colorless oil.

refractive index: n$_D^{20}$=1.5021 density: D$_4^{20}$=1.0365

After the reduction of an analytical sample using LiAlH$_4$ by analogy to Example 2 an exo/endo ratio of 84:16 was determined by gas chromatography.

Production of the aldehyde mixture ½ from TCD-ketone A (A) by modified glycidic ester synthesis To a solution of 150 g (1 mol) TCD-ketone A (A), 165.4 g (1.35 mol) ethyl chloro-acetate and 0.5 g phenothiazine in 100 ml abs. pyridine was added gradually over a period of 1 hour 81 g (1.5 mol) of sodium methylate by stirring and cooling at 15° C. After the addition of 74 g tertiary-butylmethyl ether the reaction mixture was stirred for a further 4 h at 15° C. Then with cooling at 15° C. a solution of 125 g (1.56 mol) of 50% caustic soda in 297 g methanol was added, and it was stirred overnight without further cooling. The mixture was acidified with 468 g (3.9 mol) of 50% acetic acid and slowly heated to boil point whereby there was a strong initial development of CO$_2$. After 2 h under reflux 350 g of the solvent were removed by distillation through a 20 cm Vigreux-column. The reaction mixture obtained was then diluted with 600 g of 5% NaCl solution and extracted twice with 150 ml hexane. The hexane-extract was neutralised by washing with NaHCO$_3$ solution and water and the solvent was removed in a 20 mm vacuum. 155.2 g of the raw aldehyde were obtained which after a gas chromatogram still contained 15% of the ketone A and which had an exo/endo ratio of 4:1 (as determined by gas chromatography after the reduction of an analytical sample with LiAlH$_4$ in accordance with Example 2).

For the separation of ketone A from the aldehyde mixture ½ 155 g of the raw aldehyde over a period of 30 min were dropped under stirring into a solution of 104 g NaHSO$_3$ in 2 l H$_2$O at room temperature. The suspension which was thereby formed was stirred for an additional hour at room temperature prior to two extractions with 150 ml hexane. Thereafter, the aqueous phase was rendered alkaline with 10% caustic soda and the resulting two-phase system was extracted twice with 250 ml hexane. The hexane extract was neutralised by washing with 5% NaCl solution and the solvent was removed in a 20 mm vacuum. The remaining raw product (117 g) was distilled through a 20 cm Vigreux column. 101.6 g of the aldehyde mixture ½ (62% of the th.) in the boiling range of 84°–86° C./1.5 mm were obtained as a colorless oil. GC-purity: 97.1%.

refractive index: n$_D^{20}$=1.5020 density: D$_4^{20}$=1.0366

After the reduction of an analytical sample using LiAlH$_4$ an exo/endo ratio of 80:20 was determined by gas chromatography.

EXAMPLE 4

Oxidation of the alcohol 3 from Example 2 (after separation of the alcohol 4)

A solution of 3.32 g (20 mmol) of alcohol 3 in 12 ml of abs. CH$_2$Cl$_2$ was added to a well stirred suspension of 11.3 g (30 mmol) pyridinium dichromate in 28 ml of abs. CH$_2$Cl$_2$ in a nitrogen atmosphere at 0° C. and then stirring was continued for a period of 9 h without further cooling. After dilution with 150 ml of diethyl ether the supernatant was decanted from the black residue, and the residue was washed three times each with 30 ml of diethyl ether. The combined organic solutions were filtered over a silica gel, washed with 5% hydrochloric acid, neutralised by washing with NaHCO$_3$ solution and water. The solvent was then removed in a 20 mm vacuum. After bulb tube distillation of the remaining raw product (3.19 g) under a 2 mm-vacuum 2.87 g of aldehyde 1 were obtained as a colorless oil.

GC-purity: 99.5%.

IR (film): ν=2704, 1719 cm$^{-1}$ (aldehyde).

$^1$H-NMR (300 MHz, CDCl$_3$): δ=0.85–1.05 (m, 3H), 1.12–1.33 (m, 3H), 1.61–1.69 (m, 1H), 1.81–1.97 (m, 5H), 2.04–2.09 (m, 1H), 2.22–2.28 (m, 1H), 2.32 (br. "s", 1H), 9.66 ppm (d, J=1.5 Hz, 1H, CHO).

$^{13}$C-NMR (75 MHz, CDCl$_3$): δ=27.3 (t), 29.5 (t), 30.1 (t), 31.9 (t), 32.1 (t), 40.4 (d), 42.2 (d), 48.10 (d), 48.13 (d), 54.3 (d), 203.2 ppm (d).

MS: m/z (%)=164 (4, M$^+$), 135 (61), 108 (32), 107 (100), 106 (21), 93 (27), 91 (20), 79 (58), 77 (20), 67 (88), 41 (28), 39 (21).

Oxidation of the alcohol 4 from Example 2 (after the separation of alcohol 3)

Alcohol 4 was converted into the aldehyde 2 analogously as described under a). GC-purity: 98.1%.

IR (film): ν=2710, 1719 cm$^{-1}$ (aldehyde).

$^1$H-NMR (300 MHz, CDCl$_2$): δ=0.85–1.04 (m, 2H), 1.07–1.22 (m, 2H), 1.50–1.66 (m, 4H), 1.74–1.96 (m, 4H), 2.04–2.08 (m, 1H), 2.48–2.51 (m, 1H), 2.65–2.72 (m, 1H), 9.79 ppm (d, J=1 Hz, 1H, CHO).

$^{13}$C-NMR (75 MHz, CDCl$_3$): δ=26.9 (t), 28.7 (t), 32.3 (t), 32.6 (t), 33.8 (t), 41.7 (d), 42.7 (d), 43.0 (d), 48.1 (d), 53.3 (d), 205.0 ppm (d).

MS: m/z (%)=164 (3, M$^+$), 120 (100), 118 (16), 107 (22), 92 (17), 91 (31), 79 (44), 77 (16), 67 (28), 41 (20), 39 (16).

EXAMPLE 5

Production of 8-exo/endo-formyl-2,6-exo-tricyclo[5.2.1.0$^{2,6}$]decane (½) from 8-formyl-2,6-exo-tricyclo[5.2.1.0$^{2,6}$]decene-3(4) (6) by hydration A solution of 370 g (2.28 mol) of aldehyde mixture 6 (obtained by region-selective hydroformylation of 5) in 185 g of methanol were mixed with 5 g Na$_2$CO$_3$ and 1 g palladium on activated carbon (5% Pd) and stirred for a period of 4 h in a hydrogen atmosphere at 20 bar and 45°–55° C. (use of H$_2$: 102% of the theoretical). After filtration and concentration, the hydrogenated mixture was dissolved in 100 g of hexane, neutralised by washing with H$_2$O and again concentrated. The remaining raw product (375 g) was distilled through a 1 m Vigreux-column. 327.4 g of the aldehyde mixture ½ were obtained (87.4% of the theoretical) in the boiling range of 84°–86° C./1.5 mm as a colorless oil. GC-purity: 98.5%.

After the reduction of an analytical sample using LiAlH$_4$ an exo/endo ratio of 81:19 was determined by gas chromatography.

EXAMPLE 6

Production of 8-exo/endo-formyl-2,6-exo-tri-cyclo[5.2.1.0$^{2,6}$]decane (½) from 2,6-exo-tricyclo[5.2.1.0$^{2,6}$]decene-3 (7) by hydroformylation A solution of 402 g (3 mol) of olefin 7 in 400 g of toluene was mixed with a solution of 75 mg of dimeric rhodium(II)-2-ethyl-hexanoate in 20 ml toluene and stirred under a synthesis gas atmosphere (mol ratio CO/H$_2$=1:1) for a period of 3 h at 100° C. and 180–200 bar (use of synthesis gas: 96.5% of the th.). After cooling to 30° C. the reaction mixture was separated from the solvent by distillation at 130 mbar and from the catalyst at 2 mbar. The remaining raw product (486 g) was finely distilled as described in Example 5. 440.8 g of the aldehyde mixture ½ (89.6% of the theoretical) were obtained as a colorless oil. GC-purity: 99.2%.

After reduction of an analytical probe using LiAlH$_4$ an exo/endo ratio of 11:1 was determined with gas chromatography.

EXAMPLE 7

Determination of the strength of the scent of aldehyde mixtures ½

For the evaluation of the scent, solutions of the aldehyde mixture ½ were prepared which contained the different isomeric ratios obtained by the different processes. In each case the solvent was isopropyl myristate. In a series of dilutions a 1% solution of the test sample was in each case further diluted with isopropyl myristate in a 1:10 ratio.

The test panel consisting of perfumiers determined the dilution at which a scent could no longer be noticed. The concentration for the respective threshold value for the scent is marked by underlining.

Thereby it was found that the 8-exo-enriched aldehyde-mixtures ½ were still noticeable, meaning they had a higher scent intensity, at a much higher dilution than the product produced by the known process (Example 1).

| ½(58:40) according to Example 1 | ½(84:16) according to Example 3a | ½(81:19) according to Example 5 | ½(80:20) according to Example 3b |
|---|---|---|---|
| 1% | 1% | 1% | 1% |
| 0.1% | 0.1% | 0.1% | 0.1% |
| 0.01% | 0.01% | 0.01% | 0.01% |
| 0.001% | 0.001% | 0.001% | 0.001% |
| <u>0.0001%</u> | 0.0001% | 0.0001% | 0.0001% |
| 0.00001% | 0.00001% | <u>0.00001%</u> | <u>0.00001%</u> |
| 0.000001% | <u>0.000001%</u> | .000001% | 0.000001% |

EXAMPLE 8

| Perfume formulation | a | b | c |
|---|---|---|---|
| Dihydro myrcenol | 150 | 150 | 150 |
| Patchouli oil, indonesian | 100 | 100 | 100 |
| Timberol* | 100 | 100 | 100 |
| Aldehyde D (according to Example 1) | — | 5 | — |
| Formyltricyclo-decane ½ (according to Example 3a) | — | — | 5 |
| Dipropylene glycol | 645 | 645 | 645 |

*DRAGOCO product

The mixture a is a perfume formulation having woody, flowery and sweet-herbal aspects. By the addition of 0.5% of aldehyde D (mixture b) the arrangement is more harmonic with concomitant emphasis on the green-flowery aspects. Through an alternative addition of 0.5% formyltricyclo-decane ½ (mixture c) an arrangement is obtained which is stronger than (b) and which at the same time smells fresher flowery.

EXAMPLE 9

| Perfume oil of the Chypre-type | a | b |
|---|---|---|
| oil of basil | 1.5 | 1.5 |
| oil of galbanum | 4.5 | 4.5 |
| dimethylbenzyl carbinyl acetate | 7.5 | 7.5 |
| Jasmine base* | 30.0 | 30.0 |
| mandarin oil | 30.0 | 30.0 |
| hexyl cinnamic aldehyde | 45.0 | 45.0 |
| Lignofix* | 45.0 | 45.0 |
| musk ketone | 45.0 | 45.0 |
| vetiveryl acetate | 60.0 | 60.0 |
| linalyl acetate | 90.0 | 90.0 |
| cis-3-hexenyl salicylate | 90.0 | 90.0 |
| phenylethyl alcohol | 90.0 | 90.0 |
| methyl ionone, gamma | 75.0 | 75.0 |
| benzyl salicylate | 109.0 | 109.0 |
| bergamot oil | 120.0 | 120.0 |
| Lyral** | 150.0 | 150.0 |
| formyltricyclo-decane ½ (according to Example 3a) | — | 7.5 |

*DRAGOCO-product
**IFF-product

The mixture a has a well-balanced scent of the chypre-type having aspects of agrumen. By addition of 0.75% of formyltricyclo-decane ½ (mixture b) the scent impression shifts in a very desirable way into a fresh-flowery direction with an emphasis of the underlying green-spicy note.

EXAMPLE 10

| Perfume oil for detergents | | |
|---|---|---|
| | a | b |
| Sandranol* | 5 | 5 |
| styrenyl acetate | 10 | 10 |
| aldehyde C14 | 10 | 10 |
| Rose-oxide D* 10% | 10 | 10 |
| Cyclogalbanate* | 15 | 15 |
| Isodamascon* 1% | 20 | 20 |
| Buccoxime* 1% | 20 | 20 |
| citronellol | 20 | 20 |
| hexyl salicylate | 20 | 20 |
| Ketofix* | 20 | 20 |
| Veticol acetate* | 25 | 25 |
| geraniol | 30 | 30 |
| Lilial*** | 50 | 50 |
| phenylethyl alcohol | 50 | 50 |
| Greenyl acetate* | 50 | 50 |
| benzyl acetate | 60 | 60 |
| Greenyl propionate* | 60 | 60 |
| Lignofix* | 60 | 60 |
| benzyl salicylate | 70 | 70 |
| methyl ionone, gamma | 70 | 70 |
| Galaxolide **, 50% | 100 | 100 |
| hexyl cinnamic aldehyde alpha | 100 | 100 |
| Lyral ** | 105 | 105 |
| dipropylene glycol | 15 | 15 |
| formyltricyclo-decane ½ (according to Example 3a) | — | 5 |

*DRAGOCO - product
** IFF-product
***Givaudan-product

The mixture a shows a balanced sweet-flowery tone, which is well suited for adding perfume to detergents and fabric softeners. By addition of 0.5% formyltricyclo-decane ½ mixture b is obtained having a "softer" scent impression. The flowery-caring impression in both cases is also noticeable on the washed textiles after one wash, whereby in the mixture b the flowery-fresh note is emphasised.

We claim:

1. 8-exo-Formyl-2,6-exo-tricyclo [5.2.1.0$^{2,6}$]decane (1)

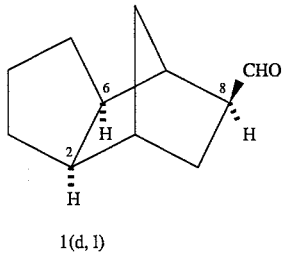

1(d, l)

2. A process for the production of a scent product having a fresh-green note and high stability, said process comprising transforming 8-exo/endo-formyl-2,6-exo-tricyclo [5.2.1.0$^{2,6}$]decane (exo/endo ratio=1.45:1) into an aldehyde mixture having an increased C-8-exo-ratio of at least exo/endo=5.25:1 using base catalysis.

3. A process for the production of a scent product having a fresh-green note and high stability, wherein 2,6-exo-tricyclo-[5.2.1.0$^{2,6}$]decene-8 is hydroformylated to 8-exo-formyl-2,6-exo-tricyclo-[ 5.2.1.0$^{2,6}$]decane (1).

4. A process for the production of a scent product having a fresh-green note and high stability, wherein the process products in accordance with claim 2, are reduced to the corresponding alcohol mixture from which the 8-exo-configuration methylol is isolated by chromatographic or distillation methods and wherein there is an oxidation to form pure 8-exo-formyl-2,6-exo-tricyclo-[ 5.2.1.0$^{2,6}$]decane 1.

5. The use of 8-exo-formyl-2,6-exo-tricyclo [5.2.1.0$^{2,6}$] decane (1) as a scent or a component of scent mixtures.

6. The use of 8-exo-enriched mixtures of 8-exo/endo-formyl- 2,6-exo-tricyclo[5.2.1.0$^{2,6}$]decane having an exo-isomer proportion of at least 70% and an endo-isomer proportion of at most 30% used as scent-imparting agent or as a component of perfume oil compositions, for cosmetic and technical uses.

7. A process for producing a scent product having a fresh-green note and high stability, said process comprising subjecting 8-endo/exo-formyl- 2,6-exo-tricyclo[5.2.1.0$^{2,6}$] decene-3 to catalytic hydrogenation to form 8-endo/exo-formyl-2,6-exo-tricyclo-[ 5.2.1.0$^{2,6}$]decane.

8. A process for the production of a scent product having a fresh-green note and high stability, wherein the process products in accordance with claim 7 are reduced to the corresponding alcohol mixture from which the 8-exo-configuration methylol is isolated by chromatographic or distillation methods and wherein there is an oxidation to 8-exo-formyl- 2,6-exo-tricyclo- [5.2.1.0$^{2,6}$]decane 1.

9. A process for the production of a scent product having a fresh-green note and high stability, wherein the process products in accordance with claim 3 are reduced to the corresponding alcohol mixture from which the 8-exo-configuration methylol is isolated by chromatographic or distillation methods and that there is an oxidation to pure 8-exo-formyl-2,6-exo-tricyclo[ 5.2.1.0$^{2,6}$]decane 1.

10. A process as in claim 2, wherein said base catalysis is by means of an aqueous methanolic solution of caustic soda at boiling temperature.

11. A process as in claim 7, wherein said catalyst is palladium carbon.

12. An aromatic composition comprising 8-exo-formyl-2,6-exo-tricyclo [5.2.1.0$^{2.6}$]decane and 8-endo-formyl-2,6-exo-tricyclo [5.2.1.0$^{2.6}$]decane, wherein the C8 exo:endo isomer ratio is at least 70:30.

13. An aromatic composition as in claim 12, wherein the C8 exo:endo isomer ratio is at least 80:20.

* * * * *